US012642470B2

(12) United States Patent
Grob et al.

(10) Patent No.: US 12,642,470 B2
(45) Date of Patent: Jun. 2, 2026

(54) WEARABLE DEVICE

(71) Applicant: NATUURWETENSCHAPPELIJK ONDERZOEK TNO (DEN HAAG), The Hague (NL)

(72) Inventors: Timon Rutger Grob, Geldrop (NL); Ozgur Tasar, Eindhoven (NL); Elise Claude Valentine Talgorn, Eindhoven (NL); Lieven Adriaenssen, Vilvoorde (BE); Marco Barink, Eindhoven (NL); Edsger Constant Pieter Smits, Eindhoven (NL); Jeroen Van Den Brand, Goirle (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 768 days.

(21) Appl. No.: 16/972,365

(22) PCT Filed: May 28, 2019

(86) PCT No.: PCT/EP2019/063709
§ 371 (c)(1),
(2) Date: Dec. 4, 2020

(87) PCT Pub. No.: WO2019/233807
PCT Pub. Date: Dec. 12, 2019

(65) Prior Publication Data
US 2021/0236036 A1     Aug. 5, 2021

(30) Foreign Application Priority Data
Jun. 7, 2018     (EP) ..................................... 18176595

(51) Int. Cl.
| A61B 5/259 | (2021.01) |
| A61B 5/00 | (2006.01) |
| A61B 5/024 | (2006.01) |

(52) U.S. Cl.
CPC ............ *A61B 5/259* (2021.01); *A61B 5/0004* (2013.01); *A61B 5/02416* (2013.01);
(Continued)

(58) Field of Classification Search
CPC ... A61B 5/0004; A61B 5/02416; A61B 5/259; A61B 5/318; A61B 5/369; A61B 5/72; A61B 2562/166
See application file for complete search history.

(56) References Cited

U.S. PATENT DOCUMENTS

| 9,378,450 B1 * | 6/2016 | Mei .................. G06K 19/07722 |
| 2008/0275327 A1 * | 11/2008 | Faarbaek ............. A61B 5/6833 |
| | | 600/382 |

(Continued)

FOREIGN PATENT DOCUMENTS

| CN | 106716717 A | 5/2017 |
| CN | 107003774 A | 8/2017 |

(Continued)

OTHER PUBLICATIONS

Wei, P. et al., "A stretchable and flexible system for skin-mounted measurement of motion tracking and physiological signals", 2014, 36th Annual International Conference of the IEEE Engineering in Medicine and Biology Society.

(Continued)

*Primary Examiner* — Bradford C. Blaise
(74) *Attorney, Agent, or Firm* — Leydig, Voit & Mayer, Ltd.

(57) ABSTRACT
A wearable system is for mounting against the skin of a subject. It comprises a flexible circuit board sandwiched
(Continued)

(e.g. laminated) between a top layer and a base layer. The flexible circuit board has a meander section between end pads. The base layer and the top layer are bonded together by a bonding layer which has a meander opening around the meander section. This means the stretchability of the meander section is not inhibited by the lamination process.

15 Claims, 3 Drawing Sheets

(52) U.S. Cl.
CPC .............. *A61B 5/6833* (2013.01); *A61B 5/72* (2013.01); *A61B 2560/0214* (2013.01); *A61B 2562/0219* (2013.01); *A61B 2562/0271* (2013.01); *A61B 2562/166* (2013.01)

(56) References Cited

U.S. PATENT DOCUMENTS

| | | |
|---|---|---|
| 2014/0039290 A1 | 2/2014 | De Graff et al. |
| 2016/0242654 A1* | 8/2016 | Quinlan ................ A61B 5/1118 |
| 2016/0317057 A1* | 11/2016 | Li ........................ A61B 5/6833 |
| 2018/0028071 A1 | 2/2018 | Shi |

FOREIGN PATENT DOCUMENTS

| | | |
|---|---|---|
| CN | 206366131 U | 8/2017 |
| CN | 107170776 A | 9/2017 |
| WO | 2015077559 A1 | 5/2015 |
| WO | 2018017205 A1 | 1/2018 |

OTHER PUBLICATIONS

Raj, M. et al., "Soft bio-integrated systems for continuous health monitoring", Visual Communications and Image Processing, 2004, vol. 9083.

Tripathi, R. et al., "Design and Fabrication of a Nano Patch Electrode for ECG using CNT/PDMS", 2017 International Conference on Computing Methodologies and Communication, Jul. 2017.

Howe, L. et al., "Mechanical testing and prototyping of laminates for superior stickto-skin sensors", Philips Technical Note PR-TN 2016/00112, Oct. 2016.

International Search Report and Written Opinion, International Application No. PCT/EP2019/063709, Mailed on Jul. 30, 2019.

Chinese National Intellectual Property Administration, Decision to Grant in corresponding Chinese Patent Application No. 201980038430.3 dated Feb. 13, 2025.

* cited by examiner

WEARABLE DEVICE

This application is the U.S. National Phase application under 35 U.S.C. § 371 of International Application No. PCT/EP2019/063709, filed on 28 May 2019, which claims the benefit of European Application Serial No. 18176595.9, filed 7 Jun. 2018. These applications are hereby incorporated by reference herein.

FIELD OF THE INVENTION

This invention relates to wearable devices such as actuators or sensors. For example, the invention is of interest for sensors for measuring one or more physiological parameters of a subject, wherein the sensor can be worn by the subject. For example, the invention relates to a wearable patch which may implement a photoplethysmographic (PPG) sensor, an electrocardiogram (EGC) sensor, an electroencephalogram sensor (EEG), a wearable ultrasound sensor (US), a wearable heart rate sensor, a wearable galvanic skin response sensor (GSR) or a motion sensor.

BACKGROUND OF THE INVENTION

Monitoring of physiological parameters is of increasing interest, to allow for better diagnosis and patient monitoring. It is for example known to provide wearable monitoring devices, such as patches, that subjects can wear in low acuity settings such as the general ward and at home. Better monitoring in general wards is needed to reduce the mortality rate. Also, accountable care drives the need to discharge patients to their home, and continue a level of monitoring at home for a period of time, typically up to 30 days.

In general, patch comfort is very important, especially in the home monitoring context where it will influence patient adherence. In addition to comfort, reliability of a wearable sensor is important in order to reach the desired period (e.g. 30 days) of home monitoring.

Wearable devices are convenient to use as they offer increased freedom of movement for the user whilst a physiological parameter is being monitored. In this way, it is possible to measure physiological parameters in a variety of circumstances, for example at different levels of physical exertion of the subject.

The physiological parameter sensor may be mounted to the user differently in different applications. The position of the mounted physiological parameter sensor relative to the subject depends on the type of physiological parameter sensor, and/or the circumstances in which physiological sensing takes place. In general, the physiological parameter sensor should be in contact with the skin but there are other cases in which a physiological parameter sensor should be separated from the subject's body.

For instance, in PPG monitoring, a steady distance between a light sensor and the skin is desired for optimal stability of the sensor signal. For ultrasound transducer patches, good contact with the skin is imperative for high quality images. Similarly, the electrodes of ECG monitoring devices or GSR sensors should be in contact with the skin.

Many sensor designs make use of multiple sensing locations of the skin, for example so that electrical conductivity can be measured between those points, or so that different signal timings at different locations can be determined. A sensor system which employs multiple different sensing modalities may also have multiple sensing locations.

This invention relates in particular to wearable systems which make use of contact locations for sensing or actuation. The multiple locations may for example relate to monitoring of a single physiological parameter, or multiple parameters. There is a need to enable these multiple sensor or actuation locations to move relative to each other, so that the body to which they are attached is able to move, for example due to breathing, the heart pulse, or just general body movement of the subject wearing the sensor system.

Generally, these different locations need to be able to communicate electrically with each other, for example so that a single processing site can gather sensing data from the multiple areas. This requires connecting conductive tracks between the contact locations. It is known to provide these connecting conductive tracks as meander paths, to provide a degree of stretchability. Flexibility and stretchability are key for comfort and for good skin contact.

A flexible printed circuit board (PCB) including a meander interconnect may for example be provided. Specific meander shapes can be used to minimize the force needed to stretch in 3D while minimizing the stress at critical points, hence minimizing chances of cracking or breaking.

The PCB may for example be encapsulated in an outer housing, together with the sensor circuitry, to form a sensor patch.

It is known for example for the PCB to be encapsulated. However, a preferred manufacturing process is a lamination process. Laminated sensor patches are for example built of layers manufactured mainly by a reel-to-reel process.

However, the reliability of the interconnect provided by the meandering PCB reduces when the meanders are more constrained by lamination. In particular stretching capability provided by the meandering section is limited. There is therefore a need for an improved design for a wearable device, such as for use as a wearable sensor patch.

SUMMARY OF THE INVENTION

The invention is defined by the claims.

According to examples in accordance with an aspect of the invention, there is provided a wearable system for mounting against the skin of a subject, comprising:
a base layer;
a flexible circuit board comprising:
    a first end pad having a first contact area facing the base layer;
    a second end pad having a second contact area facing the base layer; and
    a flexible meander section between the first and second end pads; and
a top layer, wherein the flexible circuit board is sandwiched between the base layer and the top layer,
wherein the base layer and the top layer are bonded together by a bonding layer which has a meander opening around the flexible meander section.

This system has two (or more) pads for contacting the skin of a subject or for positioning in close proximity to the skin of the subject, for example for taking readings of one or more physiological parameters, in particular which (either individually or together) require two or more contact points. It may instead be for providing signals to the skin. The two pads are connected by a meander section which gives stretchability to the system, so that it can adapt to the shape of the subject, which may also evolve as the subject moves. The meander section is in a non-bonded region so that the out of plane flexing of the meander section is not inhibited by coupling to the top layer and/or to the base layer. The deformation is thus not enforced by and/or constrained by the top and/or the base layer.

This arrangement gives increased freedom of deformation of the meander section, and this increases the reliability of the interconnection significantly. A completely free-standing interconnect gives usability issues, for example the interconnect may be damaged due to snagging behind something, e.g. clothing. Thus, the invention provides encapsulation (e.g. by lamination) between the top and base layers, but without adhesion in the region of the meander section.

The base layer may comprise first and second base layer openings beneath the first and second contact areas. These enable direct access to the pad contact areas. This is of interest if direct galvanic contact is desired with the skin. This depends on the type of sensor or actuator. For example, indirect contact may be sufficient for a capacitive sensor or movement sensor, whereas direct contact may be desired for a skin resistance sensor or ECG sensor.

The system may then comprise a first skin contact electrode and a second skin contact electrode in the first and second openings, which connect to the first and second contact areas. These may project out of the plane of the base layer to provide protruding contact electrodes. The first and second skin contact electrodes for example comprise gel electrodes.

The bonding layer may also comprise first and second bonding layer openings corresponding to the first and second base layer openings. When the bonding layer is beneath the flexible circuit board (i.e. between the circuit board and the base layer), these openings again allow direct contact with the contact areas of the end pads. However, the bonding layer may instead be above the circuit board (i.e. between the circuit board and the top layer) in which case the openings are not required.

The bonding layer may comprise contact anchors within the meander opening. These may for example make connections in the meander spaces, so that they increase the overall structural unity of the system but without constraining movement of the meander section.

The first end pad may have a first circuit area on the opposite side to the first contact area, and the second end pad may have a second circuit area on the opposite side to the second contact area.

A battery may be provided on the first circuit area and a signal processing circuit may be provided on the second circuit area. One of the first and/or second circuit areas may for example comprise a wireless communications circuit. Thus, the required circuit components may be shared between the available areas. The electrical functions for example include local battery power, local memory storage, wireless signal transmission (and optionally also signal reception, for example for receiving a command to perform sensing, or to download stored sensor data), and optionally sensor signal processing. One of the first and second circuit areas may also comprise a display device to enable sensor information to be read out directly instead of, or as well as, being stored and/or communicated to an external device.

The meander section preferably carries only interconnect tracks. In particular, the flexible meander section preferably comprises an electrical connection between the first and second end pads.

The bonding layer may comprise a hot-melt layer, a pressure sensitive adhesive, a UV-curable adhesive or a double sided adhesive tape. It is for example used to connect the top and base layers as part of a thermal lamination process.

The device preferably comprises a wearable sensor patch. There may be three or more end pads, interconnected by two or more flexible meander sections.

The sensor system for example comprises one (or more) from the list of:
    an ECG sensor;
    a PPG sensor;
    an EEG sensor;
    a GSR sensor;
    a thermistor temperature sensor;
    an accelerometer.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
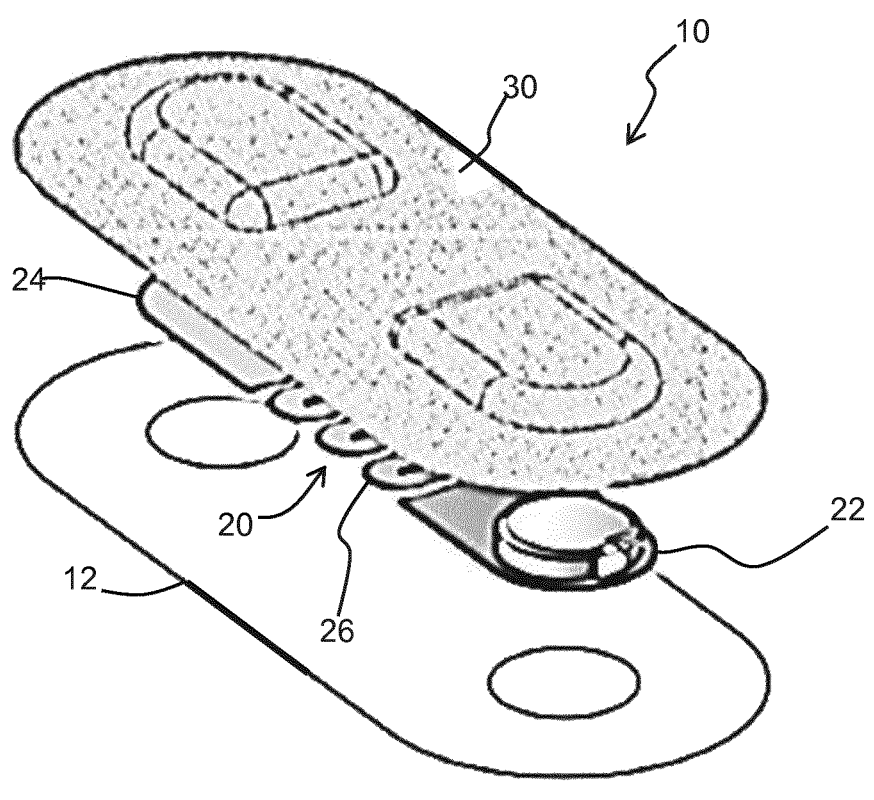
FIG. 1 shows a known sensor patch.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a wearable system such as a sensor system for mounting against the skin of a subject. It comprises a flexible circuit board sandwiched (e.g. laminated) between a top layer and a base layer. The flexible circuit board has a meander section between end pads. The base layer and the top layer are bonded together by a bonding layer which has a meander opening around the meander section. This means the stretchability of the meander section is not inhibited by the lamination process.

FIG. 1 shows a known sensor patch 10, comprising a base layer 12, a flexible circuit board 20 and a top layer 30. The flexible circuit board 20 has two end pads 22, 24 which are interconnected by a meander section 26.

The three layers shown are laminated together to form a sealed patch.

Figure 2:
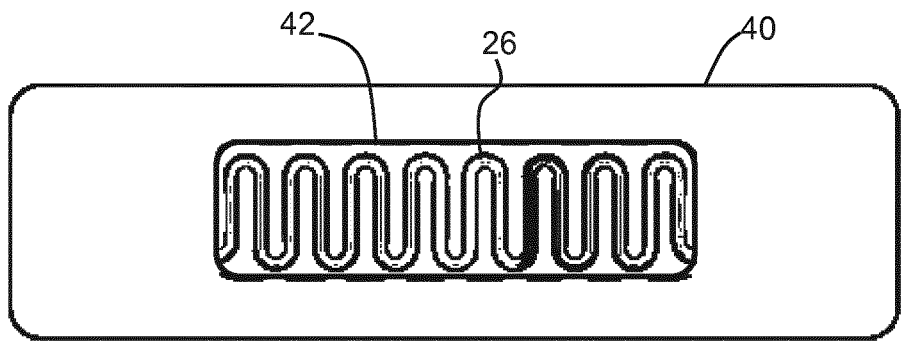
FIG. 2 shows in simplified form the design of the bonding layer used for a sensor patch in accordance with one example of the invention.

FIG. 2 shows in simplified form a design of the bonding layer used in the lamination process for a sensor system in accordance with an example of the invention. In this example, the bonding layer 40 is to be provided over the flexible circuit board. The bonding layer 40 has an opening 42 over the meander section 26 so that the meander section is not constrained by the lamination process. FIG. 2 shows the meander section 26 beneath the bonding layer, seen through the opening 42, for clarity.

Figure 3:
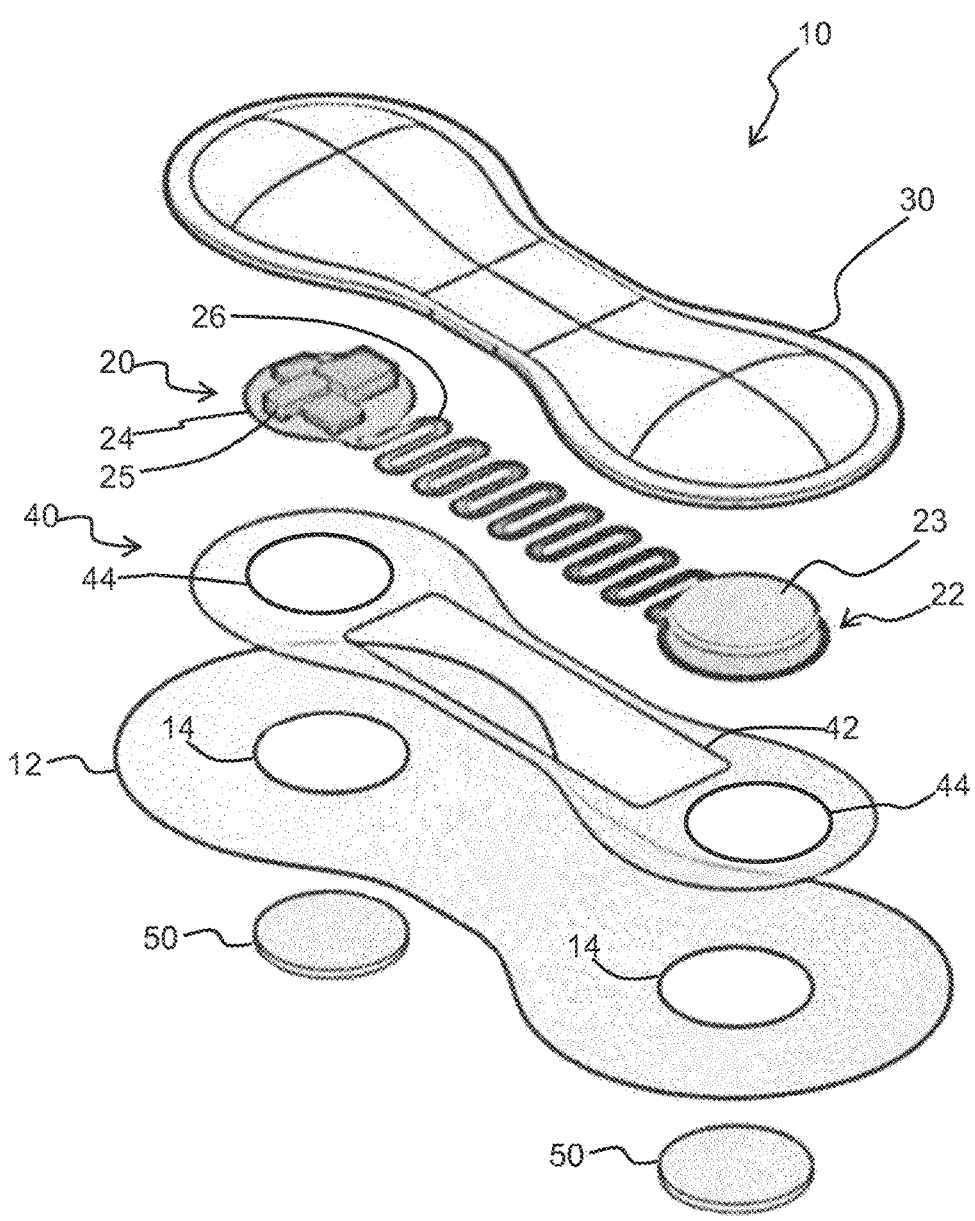
FIG. 3 shows an example of sensor system, in exploded view.

FIG. 3 shows an example of wearable system, in exploded view.

The wearable system comprises a base layer 12, a flexible circuit board 20, a top layer 30 and the bonding layer 40 with a meander opening 42. In this example, the bonding layer is beneath the flexible circuit board, namely between the flexible circuit board and the base layer. Bonding can additionally or alternatively be provided between the top layer and the flexible circuit board, again excluding the meander section. Thus, the bonding may be provided above and/or below the flexible circuit board.

Figure 4:
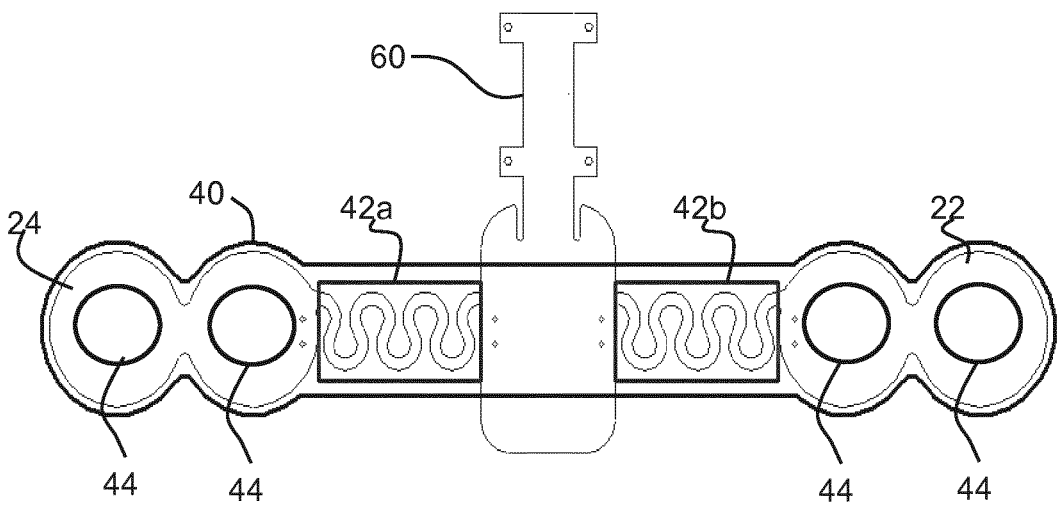
FIG. 4 shows a variation to the design of the bonding layer.

The flexible circuit board 20 comprises a first end pad 22 having a first contact area facing the base layer (and hence not seen in FIG. 4). The opposite side of the first contact area may in one example comprise a first circuit area, which for example provides connections to a battery 23.

A second end pad 24 has a second contact area facing the base layer (again not seen in FIG. 3). The opposite side of the second contact area may in one example comprise a second circuit area, which for example provides connections to sensor processing circuitry and wireless transmission circuitry 25.

This flexible circuit board may comprise a conventional polyimide flexible PCB, but it may also comprise screen-printed or inkjet-printed circuitry on a bendable polymer substrate such as polyethylene naphthalate (PEN) or polyethylene terephthalate (PET).

The meander section 26 is between the first and second end pads and it provides electrical connections between the circuitry carried by the end pads, as well as providing connections to and the contact areas of the end pads. The meander section preferably carries only interconnect tracks. In particular, the meander section preferably comprises an electrical connection between the first and second end pads.

The flexible circuit board is for example a double-sided board, with contact areas facing the base layer which function as sensor input pads or actuator output pads, and electrical tracks facing the top layer which function as connection lines and contact pads for circuit components.

In the example shown in FIG. 3, the contact areas on the underside of the end pads are for making direct galvanic contact with the skin. The base layer 12 has openings 14 aligned with the contact areas, and the bonding layer 40 also has corresponding openings 44.

To provide an interface between the skin and the contact areas, gel contact electrodes 50 can be provided. These fit in the openings 14 and 44 so that skin contact pads extend beyond the plane of the base layer 12.

The most basic design has two pads for contacting the skin of the subject, but there may be three or more pads, interconnected with each other by meander sections. The meander section is in a non-bonded region so that the stretching of the meander section is not inhibited by coupling to the top layer or base layer. In this way, there is increased freedom of deformation of the meander section.

The meander section is preferably planar and defines an undulating track in that plane, for example a sequence of alternate U-bends as shown. However, other meandering paths may be formed, for example which overall follow a straight path or a curved path.

The bonding layer may simply be around the outer edge of the overall wearable system outer housing, so that that openings 42, 44 are formed as a single opening.

However, the bonding layer preferably surrounds or covers (from above or below) the end pads so that each end pad is formed into its own enclosure. Thus, in the example of FIG. 3, there is a region of the bonding layer fully around each opening 44, and in the example of FIG. 2 the bonding layer fully covers each end pad. This provides better scaling for the circuit components.

The meander opening may be a rectangle corresponding to the outer envelope shape of the meander section. However, other shapes may be used. The meander opening may fully surround the meander section 26 but there may be portions of the meander section which are covered by the bonding layer, such as the ends.

FIG. 4 shows a variation to the design of the bonding layer 40. The end pads are each formed as a double circle to enable increased contact area. The circuitry may for example all be on one side of the flexible circuit board, facing downwardly. A central area 60 provides a connection to a non-flex printed circuit board.

The meander opening 42 is formed as two sections 42a, 42b, one on each side of the central area 60.

Figure 5:
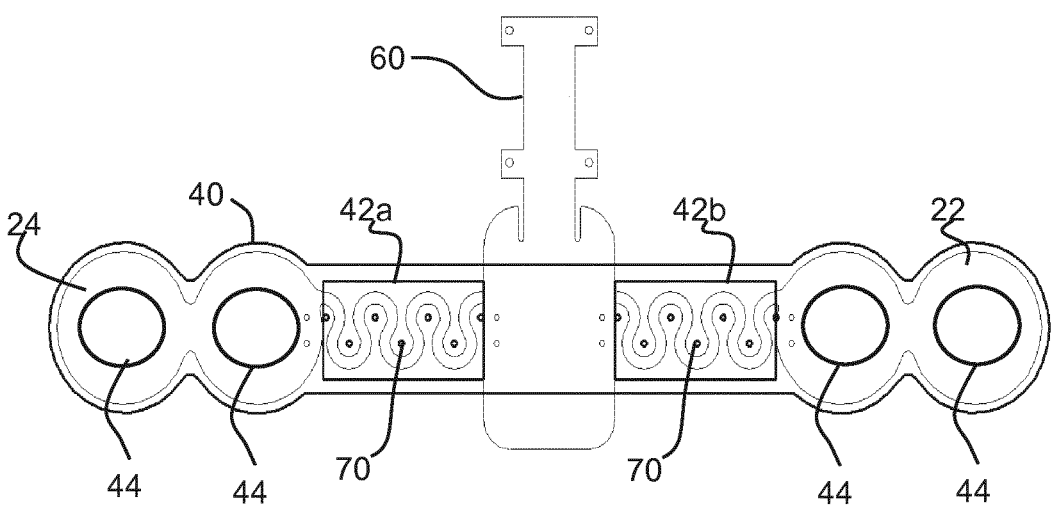
FIG. 5 shows a modification to the design of the bonding layer of FIG. 4.

FIG. 5 shows a modification to the design of the bonding layer of FIG. 4. The bonding layer 40 has contact anchors 70 within the meander openings 42a, 42b. These make connections between the top layer and base layer in the spaces between the meandering path of the circuit board. The overall structural unity of the system is improved but without constraining movement of the meander section.

The bonding layer may be a hot-melt layer for thermal curing during lamination, such as a polyurethane film, or another adhesive for example using a silicone adhesive, a polyurethane adhesive or an acrylic adhesive. Adhesive foams may also be used.

The top layer 30 is for example a foam structure, such as a thermoform foam structure. It has a shape to provide housing areas for the circuit components.

The flexible circuit board 20 is for example a polyimide flexible foil (e.g. with thickness of tens of microns) with a copper conductor layer (e.g. also with thickness of ones or tens of microns).

The base layer 12 comprises a liner of silicone or thermoplastic polyurethane.

The contact electrodes 50 for example comprise screen printed silver chloride which are provided at the contact areas (at the bottom of the flexible circuit board). Contact electrodes may alternatively be provided using conductive adhesive.

The wearable system for example comprises one (or more) sensor types from the list of:
an ECG sensor;
a PPG sensor;
an EEG sensor;
a GSR sensor;
a thermistor temperature sensor;
an accelerometer.

The wearable system may thus be used to determine one or more of various parameters such as heart rate, respiratory rate, heart rate variability, skin temperature, body posture, fall detection and activity level (such as a steps count).

As mentioned above, the wearable system is preferably battery operated, and a battery is provided on one of the circuit areas. A signal conditioning or processing circuit and wireless communications circuit are also provided on the circuit areas. There may also be memory storage, a display device.

The invention applies to wearable sensors or actuators, and they may take the form of a patch or a textile.

The invention is not limited to physiological sensory body systems. It can also be used for example for body motion sensing. In that case the wearable sensors will not measure a physiological body parameter, but will be in the form of a gyroscope or accelerometer which determines the movement of the body. Another option is non-sensory electronics in a shirt such as lights, stretchable displays, solar cells, heating, or even certain therapy options. The meander design can be used in all of these stretchable electronics cases.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A wearable system for mounting against the skin of a subject, the wearable system comprising:
   a base layer;
   a top layer;
   a bonding layer for bonding the base layer and the top layer together; and
   a flexible circuit board sandwiched between the base layer and the top layer, the flexible circuit board comprising:
      a first end pad having a first contact area facing the base layer;
      a second end pad having a second contact area facing the base layer; and
      a flexible meander section extending along its entire length between the first end pad and the second end pad;
   wherein the bonding layer has a meander opening formed around an outer edge of the flexible meander section, and
   wherein the bonding layer is positioned between the flexible circuit board and the top or base layer such that the flexible meander section is positioned with its entire length in the meander opening in such a way that the flexible meander section is in a non-bonded region and is not constrained by the bonding so as to refrain from inhibiting stretching of the meander section by coupling to the top or base layer.

2. The system as claimed in claim 1, wherein the base layer comprises a first base layer opening and a second base layer opening, wherein the first base layer opening is beneath the first contact area and the second base layer opening is beneath the second contact area.

3. The system as claimed in claim 2, further comprising a first skin contact electrode in the first base layer opening which connects to the first contact area and a second skin contact electrode in the second base layer opening which connects to the second contact area.

4. The system as claimed in claim 3, wherein the first skin contact electrode and the second skin contact electrode comprise gel electrodes.

5. The system as claimed in claim 1, wherein the bonding layer comprises a first bonding layer opening corresponding to the first base layer opening and a second bonding layer opening corresponding to the second base layer opening.

6. The system as claimed in claim 1, wherein the bonding layer comprises contact anchors within the meander opening.

7. The system as claimed in claim 1, wherein the first end pad has a first circuit area on the opposite side to the first contact area, and the second end pad has a second circuit area on the opposite side to the second contact area.

8. The system as claimed in claim 7, further comprising a battery on the first circuit area.

9. The system as claimed in claim 7, further comprising a signal processing circuit on the second circuit area.

10. The system as claimed in claim 7, wherein one of the first circuit area and the second circuit area comprises a wireless communications circuit and/or a display device.

11. The system as claimed in claim 1, wherein the bonding layer comprises at least one of a hot-melt layer, a pressure sensitive adhesive, a UV-curable adhesive or a double sided adhesive tape.

12. The system as claimed in claim 1, wherein the flexible meander section comprises an electrical connection between the first and second end pads.

13. The system as claimed in claim 1, wherein the base layer, the top layer, the bonding layer, and the flexible circuit board form a wearable sensor patch.

14. The system as claimed in claim 1, further comprising a third end pad, wherein the second end pad and the third end pad are interconnected by a second flexible meander section.

15. The system as claimed in claim 1, further comprising at least one of an ECG sensor; a PPG sensor; an EEG sensor; a GSR sensor; a thermistor temperature sensor; or an accelerometer.

* * * * *